United States Patent [19]

Karpov et al.

[11] 4,314,475
[45] Feb. 9, 1982

[54] METHOD FOR CHECKING THERMOCATALYTIC SENSORS OF MINE SAFETY SYSTEMS

[76] Inventors: Evgeny F. Karpov, prospekt Vernadskogo, 125, kv. 167; Isaak E. Birenberg, Leningradsky prospekt, 9, kv. 25; Boris I. Basovsky, ulitsa 16 Parkovaya, 49, korpus 1, kv. 58, all of, Moscow; Vladimir V. Popov, Moskovskoi oblasti poselok VUGI, 6, kv. 18, Ljubertsy-4 Moskovskoi oblasti, all of U.S.S.R.

[21] Appl. No.: 112,139

[22] Filed: Jan. 14, 1980

Related U.S. Application Data

[63] Continuation of Ser. No. 945,919, Sep. 26, 1978, abandoned.

[30] Foreign Application Priority Data

Mar. 2, 1978 [SU] U.S.S.R. ............... 2587202

[51] Int. Cl.³ ........................................... G01N 25/32
[52] U.S. Cl. .................................. 73/27 R; 23/232 E
[58] Field of Search .................... 73/1 G, 27 R, 26; 23/232 E; 422/96

[56] References Cited

U.S. PATENT DOCUMENTS

| | | | |
|---|---|---|---|
| 2,768,069 | 10/1956 | Thompson | 23/232 E |
| 2,857,251 | 10/1958 | Krogh | 422/96 X |
| 2,951,359 | 9/1960 | Krupp | 73/1 G |
| 3,497,323 | 2/1970 | Neubert | 73/27 R X |
| 3,519,391 | 7/1970 | Winter et al. | 73/27 R X |
| 3,549,327 | 12/1970 | Fergusson | 73/27 R X |
| 3,564,474 | 2/1971 | Firth et al. | 73/27 R X |
| 3,607,084 | 9/1971 | Mackey | 73/27 R X |
| 3,644,864 | 2/1972 | Hirsbunnet et al. | 338/25 |
| 3,678,489 | 7/1972 | Scherban et al. | 73/27 R X |
| 3,924,442 | 12/1975 | Kerho et al. | 73/1 G |
| 4,036,915 | 7/1977 | Lucero et al. | 73/1 G X |

*Primary Examiner*—Daniel M. Yasich

[57] ABSTRACT

According to the invention, a maximum output signal of the sensor is measured as the sensor is actuated and voltage is applied to its sensitive element to produce a prescribed heating temperature, whereupon one measures the steady-state output signal of the sensor and the duration of the transient process between the maximum signal and the steady-state signal.

1 Claim, 2 Drawing Figures

METHOD FOR CHECKING THERMOCATALYTIC SENSORS OF MINE SAFETY SYSTEMS

This application is a continuation of application Ser. No. 945,919, filed Sept. 26, 1978, now abandoned.

Field of the Invention

The present invention relates to the control of flammable gases in mines and is applicable to remote methane concentration measuring and automatic gas protection systems based on the thermocatalytic principle. More specifically, the invention relates to checking sensors operating in mines.

BACKGROUND OF THE INVENTION

At present, gas-hazardous mines extensively use systems for remote measuring of the methane concentration in the mine atmosphere and automatic gas protection systems which, in turn, employ thermocatalytic sensors. A methane sensor is the most critical unit of such systems, therefore, periodic diagnostic checks of such sensors are necessary for effective operation of such systems. In the course of a diagnostic check of a sensor one is expected to find out if the sensor operates normally under all operating conditions; one also finds out the causes of failures and pinpoints inoperative parts and units.

Modern practice offers no diagnostic checking methods that could fully solve the problem of checking thermocatalytic methane sensors employed in remote measuring and automatic gas protection systems in mines.

There are methods which provide a partial solution to the problem by making it possible to check the correctness of readings of thermocatalytic methane sensors. This is done by comparing readings of the sensor under steady-state gas conditions with those of a gas analyzer regarded as a standard instrument, with the gas analyzer and the sensor operating in the same medium (cf. "Apparatura systemy avtomaticheskoy gazovoy zashchity i tsentralizovannogo teleavtomaticheskogo controlya methana AMT-" /"Equipment Incorporated In the Automatic Gas Protection and Centralized Remote Methane Content Measuring System of the AMT-3 Type"/, Service Manual prepared by the Krasny Metallist Electromechanical Works in Konotop, Sumy Regional Press Department, Konotop, 1971, p. 32). The known methods do not make it possible to check the performance of sensors when the methane concentration in the mine varies due to different gas dynamic factors; nor do the conventional methods make it possible to find out the causes of malfunctions and pinpoint parts and units rendered inoperative.

The existing methods cannot be carried out with the aid of remote control systems and require that the checking personnel should descend underground to inspect the sensors.

There is known a method for checking the correctness of readings of a thermocatalytic sensor of a remote methane concentration measuring and gas protection system of a mine at reference points of its calibration curve. The method comprises purging of the reaction chamber with clean air and standard methane-air mixture (cf. "Rukovodstvo po oborudovaniyu i ekspluatatsii system avtomaticheskoy gazovoy zashchity i tsentralizovannogo telecontrolya soderzhaniya methana AMT-3 na ugolnykh shakhtakh" /"AMT-3, Automatic Gas Protection and Centralized Remote Methane Concentration Measuring System for Use in Coal Mines. Description and Service Manual"/, the Ministry of Coal Industry of the USSR, Moscow, 1974, p. 33). The purging with clean air serves to check the zero position of the sensor, while the purging with methane-air mixture is used to check the readings of the sensor at one point of its calibration curve.

However, the method under review is not intended for remote-controlled supply of information, but, on the contrary, makes it necessary to transport vessels containing clean air and standard methane-air mixture to sensor locations. Besides, the checking of sensors is inadequate in that it does not include the checking of operating speed which is a vital factor determining the dynamic error of methane concentration measurements with the methane concentration varying at different rates. Nor does the method under review make it possible to find out the causes of sensor failures whereof the most frequent ones include: variations in the throughput rate of the working thermoconverter element in the course of methane oxidation due to changes of the catalytic activity of that element under the effects of mine atmosphere components which poison the catalyst, or due to other reasons; and variations in the resistance of the reaction chamber to the transfer of methane through its gaseous exchange walls which may get soiled or be affected by dust and moisture.

SUMMARY OF THE INVENTION

It is an object of the present invention to provide a method for checking a thermocatalytic sensor of a remote methane concentration measuring and gas protection system of a mine, which would make it possible to perform diagnostic checks of the sensor without using standard methane-air mixtures and pure air and without resorting to reference gas analyzers.

It is another object of the invention to provide a method for checking a thermocatalytic sensor of a remote methane concentration measuring and gas protection system of a mine, which would make it possible to check the operating speed of the sensor, a feature of utmost importance for raising the effectiveness of gas protection equipment in mines with instantaneous outburst of cool and gas.

It is still another object of the invention to provide a method for checking a thermocatalytic sensor of a remote methane concentration measuring and gas protection system of a mine, which would ensure supply of information on the throughput rate of the thermocatalytic conversion element in the course of methane oxidation, as well as on the resistance of the reaction chamber to the transfer of methane through its gas-permeable walls, and thus would make it possible to rapidly detect the causes of failures.

It is a further object of the invention to provide a method for checking a thermocatalytic sensor of a remote methane concentration measuring and gas protection system of a mine, which would provide a relatively simple solution to the problem of controlling all the checking operations from the surface.

The foregoing and other objects of the present invention are attained by providing a method for checking a thermocatalytic sensor of a remote methane concentration measuring and gas protection system of a mine, which sensor comprises a sensitive thermocatalytic element arranged in a reaction chamber with a gas-permeable wall and is permanently incorporated in the mine safety system, the method being characterized in that a maximum output signal of the sensor is measured at a moment the sensor is actuated and voltage is applied to its sensitive element to produce a prescribed heating temperature, whereupon one measures the steady-state output signal of the sensor and the duration of the transient process between the maximum and steady-state signals.

This makes it possible to determine the throughput rate of the sensitive thermocatalytic element in the course of methane oxidation, as well as the resistance of the reaction chamber walls to the transfer of methane, and thus find out the measurement error.

According to an alternative embodiment of the invention, the method for checking a thermocatalytic sensor of a remote methane concentration measuring and gas protection system of a mine is characterized in that the temperature of the thermocatalytic element of the sensor installed in the mine is reduced from a certain normal operating temperature to a level at which catalytic oxidation of methane on that element is discontinued, after which the sensor is thus left for a period of time sufficient to equalize the methane concentration in the reaction chamber of the sensor with that in the atmosphere of the mine, whereupon the temperature of the thermocatalytic element is raised to said normal operating temperature, and one measures the output signal ($S_H$) of the sensor at a moment it reassumes the working temperature, the output signal ($S_y$) after a certain period of time, and the time interval required to stabilize the output signal of the sensor following the return of temperature of the sensor's element, whereupon one determines the throughput rate of the thermocatalytic element in the course of methane oxidation, as well as the resistance of the reaction chamber to the transfer of methane through its gaseous exchange walls and the methane concentration measurement error, which is done with the use of the following expressions:

$$\gamma = \frac{S_H - S_y}{T S_H} \cdot V_k,$$

where $\gamma$ is the throughput rate of the working thermocatalytic element in the course of methane oxidation, $m^3/sec$;

$S_H$ and $S_y$ are the initial and steady-state output signal values, respectively, in the course of the transient process, V/ or A/;

$V_k$ is the cubic content of the reaction chamber, $m^3$;

$$\phi = \frac{S_H T}{S_y V_k},$$

where $\phi$ is the resistance of the reaction chamber to the transfer of methane through its gas-permeable walls, $sec/m^3$;

$$\Delta C = C - \frac{100 T S_H^2}{K V_k (S_H - S_y)},$$

where $\Delta C$ is the absolute error in measuring the methane concentration, percent by volume;

C is the methane concentration corresponding to the signal $S_H$ produced by the sensor, percent by volume;

100 is the coefficient of conversion of the volume concentration of methane from relative units to percent units, %;

K is the coefficient of conversion of the flow of methane oxidized on the working thermocatalytic element to an electric signal subject to measurement, $$\frac{V \cdot \sec}{m^3} \left( \text{or } \frac{A \cdot \sec}{m^3} \right).$$

This makes it possible to employ the method according to the invention for checking sensors in the course of their continuous operation in remote methane concentration measuring and gas protection systems of mines.

BRIEF DESCRIPTION OF THE ACCOMPANYING DRAWINGS

Other objects and advantages of the present invention will become more apparent from the following detailed description of a preferred embodiment thereof, taken in conjunction with the accompanying drawings, wherein.

DETAILED DESCRIPTION OF THE INVENTION

As stated above, the present invention is concerned with a method for checking a thermocatalytic sensor incorporated in a remote methane concentration measuring and gas protection system of a mine.

Figure 1:
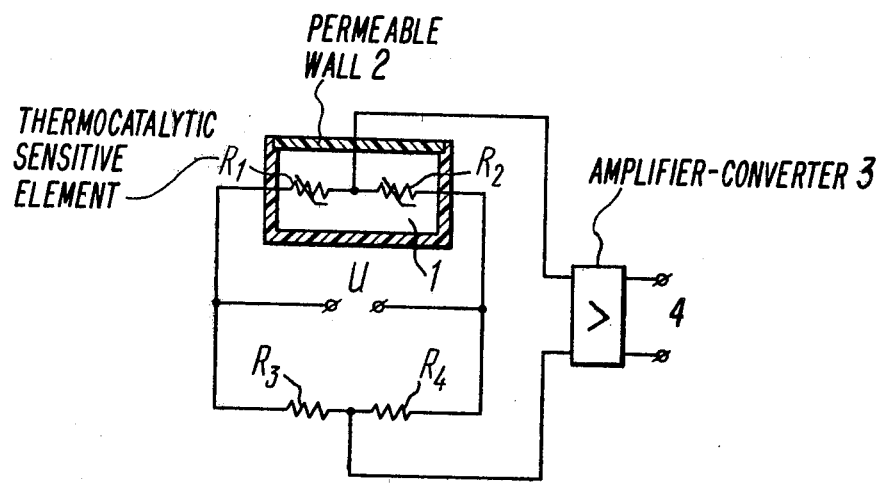
FIG. 1 is a key diagram of a device for carrying out the method in accordance with the invention.

The method is carried out with the aid of a device shown in FIG. 1, which comprises a working thermocatalytic sensitive element $R_1$ arranged in a reaction chamber 1 having a gas-permeable wall 2. The chamber 1 may also accommodate a compensation sensitive element $R_2$ whose function is to eliminate the effects on the output signal of the sensor of mine atmosphere parameters not subject to measurements. Both sensitive elements are connected in an electric comparison circuit, for example, in a bridge measuring circuit as shown in FIG. 1, whereof one arm is composed of the elements $R_1$ and $R_2$, whereas the other arm contains resistors $R_3$ and $R_4$. When in operation, the thermocatalytic sensitive element is heated by supply voltage, applied to the bridge circuit across terminals U, to a temperature at which methane oxidation takes place.

Information on the concentration of methane in the atmosphere of the mine, supplied by the sensor, may be transmitted via an amplifier-converter unit 3 from whose output 4 a measuring signal S is picked up.

Figure 2:
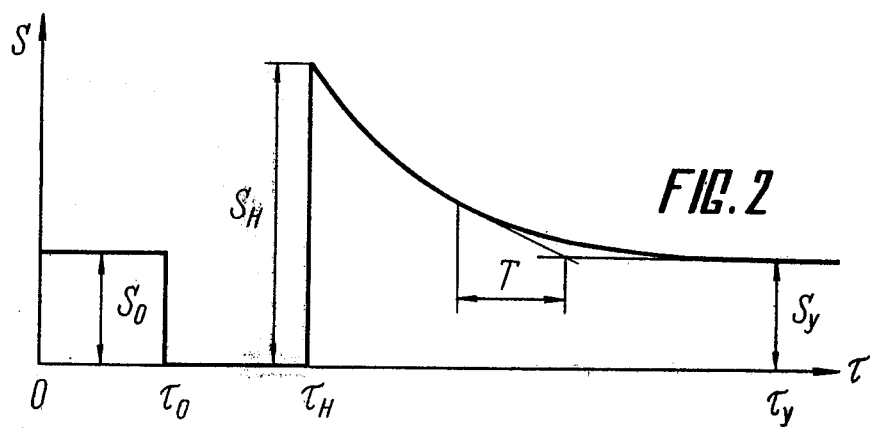
FIG. 2 is a plot showing the relationship in time between the output signal of the thermocatalytic sensor being checked and the degree of heating of its sensitive element.

The method of this invention is illustrated by the plot of FIG. 2.

The plot shows how the above-mentioned signal S varies with time. $S_o$ corresponds to the value of this signal before the sensor is put into operation, i.e. before the sensor is checked. In order to check the sensor, a telemechanic instruction is transmitted from the surface control panel, over telemechanic channels, to the sensor to reduce the temperature of the sensitive elements of the sensor to a point at which no catalytic oxidation of methane takes place. This can be done, for example, by varying the supply voltage of the sensitive elements. The sensor is then left for a period of time $\tau_o$-$\tau_H$ to equalize the methane concentration in the reaction chamber with that in the atmosphere of the mine. With no oxidation reaction underway on the thermocatalytic sensitive element, the sensor produces a steady-state signal which is used to determine the electrical zero position. At the moment $\tau_H$, a telemechanic instruction is issued to raise the temperature of the sensitive elements to a level corresponding to their normal operating conditions. The values of the initial signal $S_H$ and steady-state signal $S_y$ produced by the sensor during this transient process are recorded; the time constant T, which characterizes the operating speed of the sensor, is determined; after this one determines the throughput rate $\gamma$ of the thermocatalytic sensitive element in the course of methane oxidation, as well as the resistance $\phi$ of the reaction chamber to the transfer of methane through its gas-permeable wall, and the error in measuring the methane concentration.

The following example will serve to provide a better understanding of the present invention.

EXAMPLE

The object of diagnostic checking is a thermocatalytic sensor of a remote methane concentration measuring and automatic gas protection system of a mine, comprising a working thermocatalytic element and a compensation thermocatalytic element accommodated in a reaction chamber and connected in a bridge circuit. Each of the thermocatalytic elements is a platinum transistor with a ceramic coating whose shape approximates a sphere. The ceramic coating of the working element serves as a carrier of a catalyst consisting of platinum and palladium. No catalyst is applied onto the compensation element. The reaction chamber is defined by a hollow cylinder of a gas-tight material. One of the end faces of the cylinder is closed by an insulating plate which also serves to support the thermocatalytic elements. The opposite end face of the cylinder is closed by a gas-permeable wall of a permeable ceramic-metal material.

The sensor specification is as follows:

U—supply voltage of the bridge circuit, 2.2 V;

the initial temperature of the thermocatalytic elements, corresponding to the supply voltage of the bridge circuit (°C.), 450;

the time constant of transient processes due to variations of the methane concentration in that chamber (sec), 37.3;

the throughput rate of the thermocatalytic element in the course of methane oxidation (m$^3$/sec), 0.077.10$^{-7}$;

the resistance of the reaction chamber to the transfer of methane through the gas-permeable wall, $\phi$ (sec/m$^3$), 1.585.10$^7$; the coefficient of conversion of the flow of methane oxidized on the surface of the thermocatalytic element to an electric signal to be measured, K (V.sec/m$^3$), 39.10$^6$;

the voltage sensitivity of the sensor to methane, S $\left(\dfrac{V}{\text{percent by volume}}\right)$, 0.015 ± 10.0;

the cubic content of the reaction chamber, $V_k$(m$^3$), 6.10$^{-6}$.

The sensor is tested on a bench equipped with a gas chamber of inorganic glass, an interferometer, a loop oscillograph, a controlled power source, a voltmeter and a methane detector which is a millivoltmeter graduated in percent by volume of methane concentration.

To perform a diagnostic check, the sensor is arranged in the gas chamber and connected to the power source. A methane-air mixture is prepared in the gas chamber, the concentration of methane in the mixture being monitored with the aid of the interferometer. As this takes place, the operating value of the supply voltage is maintained across the sensor and checked by the voltmeter.

The signal produced by the sensor is checked with reference to the reading of the methane detector and recorded on the oscillogram.

As the sensor measures the methane content in the methane-air mixture, the concentration of methane in its reaction chamber is lower than that in the medium being investigated, which is due to the resistance of the gaseous exchange wall to the transfer of methane as it oxidizes on the working thermocatalytic element.

To carry on with the diagnostic check, the supply voltage is dropped almost instantaneously from 2.2 v to 1.3 v. The temperature of the thermoconverter elements drops by 450° C. to about 250° C. so that methane oxidation on the working element is discontinued. As a result, the methane concentration in the reaction chamber equalizes with that in the medium subjected to analysis. The concentrations are practically equal in about 10 minutes. After the electrical zero position is determined, the working supply voltage is brought back to normal, which the followed by recording the transient process which is an exponential process and is due to a reduced concentration of methane in the reaction chamber because of the renewed oxidation reaction.

The oscillogram of the transient process is used to determine the time constant characterizing the operating speed of the sensor, and the values of the initial output signal ($S_H$) and the steady-state output signal($S_y$), as well as to calculate the throughput rate of the working thermoconverter element in the course of methane oxidation, the resistance of the reaction chamber to the transfer of methane through its gas-permeable wall and the error in measuring the methane concentration. The above calculations are based on the following equations:

$$\gamma = \frac{S_H - S_y}{T S_H} \cdot V_k,$$

where $\gamma$ is the throughput rate of the working thermocatalytic element in the course of methane oxidation, m$^3$/sec;

$S_H$ and $S_y$ are the values of the initial output signal and the steady-state output signal, respectively, in the course of the transient process, V;

$$\phi = \frac{S_H T}{S_y V_k},$$

where $\gamma$ is the resistance of the reaction chamber to the transfer of methane through its gas-permeable walls, sec/m$^3$;

$$\Delta C = C - \frac{100\, T}{K V_k (S_H - S_y)},$$

where $\Delta C$ is the absolute error in measuring the methane concentration, percent by volume;

C is the methane concentration corresponding to the electric signal $S_H$ recorded on the oscillogram, percent by volume;

100 is the coefficient of converting the volume concentration of methane from relative units to percent units, %;

K is the coefficient of conversion of the flow of methane oxidized on the working thermocatalytic element to an electric signal to be measured, which is determined by comparison for each specific type of equipment in the course of production tests, $$\frac{V}{m^3/\text{sec}} \left( \text{or} \, \frac{A}{m^3/\text{sec}} \right).$$

The following table lists the results of diagnostic checks carried out with different concentrations of methane in methane-air mixtures prepared in the gas chamber.

systems intended to serve purposes. These advantages are as follows:

the method of this invention makes it possible to carry out diagnostic checks of sensors without using standard methane-air mixtures and pure air and without resorting to a standard gas analyzer, which provides a relatively simple solution to the problem of remote control of checking operations;

the method of this invention makes it possible to check the operating speed of sensors, a feature of vital importance for improving the effectiveness of gas protection equipment in mines with instantaneous outburst of coal and gas;

the method makes it possible to obtain information on the throughput rate of the thermocatalytic element in the course of methane oxidation and on the resistance of the reaction chamber to the transfer of methane through its gaseous exchange wall, which, in turn, ensures rapid and effective trouble shooting.

Today, thermocatalytic sensors for monitoring methane concentrations, which are used in mines all over the world, are checked with the air of standard gas mixtures contained in special vessels.

The method of the present invention provides a dramatic improvement in the checking technique. The use of the proposed method is clearly indicated by the absence in the mines of vessels for gas mixtures and equip-

TABLE

| Methane Concentration Measured by Interferometer, $C_m$, % by volume | Concentration Measured by Methane Detector Connected to Sensor, C, % by volume | Absolute Error of Sensor Determined by Direct measurement, $\Delta C = C_m$-C, % by volume | Initial Value of Output Signal in Transient Process, $S_H$, mV | Steady-State Value of Output Signal in Transient Process, $S_y$, mV | Time Constant of Transient Process, T, sec | Throughput Rate of Thermoconverter element, $\alpha$, $m^3$/sec | Resistance of Reaction Chamber to Methane Transfer, $\alpha$, sec/$m^3$ | Absolute Error of Sensor Calculated on the Basis of Proposed Method, $\Delta C$, % by volume |
|---|---|---|---|---|---|---|---|---|
| 1 | 2 | 3 | 4 | 5 | 6 | 7 | 8 | 9 |
| 0.2 | 0.2 | 0.00 | 7.74 | 3.0 | 36.4 | $1.01 \cdot 10^{-7}$ | $1.57 \cdot 10^{-7}$ | 0 |
| 0.5 | 0.48 | 0.02 | 18.8 | 7.3 | 36.8 | $1.0 \cdot 10^{-7}$ | $1.57 \cdot 10^{-7}$ | 0.018 |
| 1.0 | 0.97 | 0.03 | 37.0 | 14.5 | 37.4 | $0.975 \cdot 10^{-7}$ | $1.59 \cdot 10^{-7}$ | 0.025 |
| 1.5 | 1.4 | 0.1 | 53.5 | 21.0 | 38.2 | $0.955 \cdot 10^{-7}$ | $1.62 \cdot 10^{-7}$ | 0.06 |
| 2.0 | 1.95 | 0.05 | 75.4 | 29.2 | 36.5 | $1.0 \cdot 10^{-7}$ | $1.55 \cdot 10^{-7}$ | 0.06 |

As is seen from the table, there is very good correlation between the results of determining the absolute error of the sensor, obtained by direct measurement of methane concentration by means of an interferometer taken as a standard instrument, and data obtained with the use of the diagnostic checking method in accordance with the invention. There is also good correlation between the results of determining other parameters, such as the time constant, the throughput rate of the thermoconverter element and the resistance of the reaction chamber to the transfer of methane, with the respective values listed above in the sensor specification.

When determining parameters and the absolute measurement error with the use of the diagnostic checking method according to the invention, it is not necessary to know in advance the concentration of methane in the gas medium being investigated.

The proposed method for diagnostic checks of a thermocatalytic sensor incorporated in a remote methane content measuring and gas protection system of a mine has a number of advantages over the conventional ment for filling such vessels, as well as by the incorporation in the remote methane content measuring and gas protection systems of special devices intended to realize the method of this invention, such as voltage switches for varying the temperature of the sensitive elements and relays for metering time intervals during which the sensors operate at reduced voltage.

What is claimed is:

1. A method for checking, in a mine environment, a thermocatalytic methane sensor having a gas permeable reaction chamber housing a thermo-catalytic converting element and a supply voltage for controlling the temperature of said thermo-catalytic converting element, comprising the successive steps of:

reducing the sensor supply voltage to a level at which said thermo-catalytic converting element is cooled to a temperature obviating methane oxidation thereon;

keeping the sensor at the reduced supply voltage for a time at least equal to a period during which methane concentration in said reaction chamber is levelled out to become equal to that in the mine environment;

raising the sensor supply voltage, following the levelling out of methane concentration, stepwise to a level at which said thermo-catalytic converting element is heated to a temperature at which methane is oxidized thereon;

measuring maximum and steady-state output signals provided by the sensor and also the time constant of a transient process during which the methane concentration changes within said reaction chamber and which continues until a dynamic equilibrium is set up between methane oxidizing on said thermo-catalytic converting element and methane penetrating into said reaction chamber from the mine environment;

determining, after said measurements, efficiency of the thermo-catalytic converting element in methane oxidation, resistance of at least a wall of the reaction chamber to diffusive transfer of methane through its walls, and the sensor error in measuring methane concentration on the basis of the following expressions:

$$\gamma = \frac{S_H - S_y}{T S_H} V_K$$

where $\gamma$ is the throughput rate of the thermo-catalytic converting element in m³/sec;

$S_H$ and $S_y$ are the maximum and steady-state values of the output signals of said sensor;

$V_K$ is the volume of the reaction chamber, in cu.m.;

T is the time constant of the transient process, in seconds;

$$\phi = \frac{S_H T}{S_y V_K}$$

where $\phi$ is the resistance of said wall of the reaction chamber to the transfer of methane through its gas-permeable walls, in sec/m³;

$$\Delta C = C - \frac{100 T S_H^2}{K V_K (S_H - S_y)}$$

wherein $\Delta C$ is the absolute error in methane concentration measured by the sensor, in vol.%;

C is the methane concentration corresponding to the signal $S_H$ produced by the sensor, in vol.%;

100 is a coefficient for converting the volume concentration of methane from relative units to percentage points;

K is a coefficient of conversion of methane flow reacting on said thermo-catalytic converting element to an electric signal being measured, [Bc/m³ or Ac/m³].

* * * * *